United States Patent [19]

DeFrank et al.

[11] Patent Number: 5,066,142
[45] Date of Patent: Nov. 19, 1991

[54] PROTECTIVE APPARATUS FOR A BIOMEDICAL PROBE

[75] Inventors: Michael P. DeFrank, Temecula; Robert J. Rosati, Carlsbad, both of Calif.

[73] Assignee: IVAC Corporation, San Diego, Calif.

[21] Appl. No.: 490,333

[22] Filed: Mar. 8, 1990

[51] Int. Cl.⁵ .............................................. G01K 1/08
[52] U.S. Cl. ................................................... 374/208
[58] Field of Search ............... 374/131, 158, 208, 209; 206/306; 128/736, 664, 9

[56] References Cited

U.S. PATENT DOCUMENTS

| | | | |
|---|---|---|---|
| 2,661,454 | 12/1953 | Wannamaker, Jr. et al. | 323/66 |
| 2,696,117 | 12/1954 | Harrison | 374/133 |
| 3,277,715 | 6/1962 | Vanderschmidt | 374/9 |
| 3,282,106 | 11/1966 | Barnes | 128/664 |
| 3,368,076 | 2/1968 | Clifford | 250/83.3 |
| 3,491,596 | 1/1970 | Dean | 374/178 |
| 3,531,992 | 10/1970 | Moore | 128/736 |
| 3,581,570 | 6/1971 | Wortz | 128/736 |
| 3,878,836 | 4/1975 | Twentier | 128/9 |
| 3,942,891 | 3/1976 | Speilberger et al. | 356/43 |
| 4,005,605 | 2/1977 | Michael | 374/129 |
| 4,301,682 | 11/1981 | Everest | 374/112 |
| 4,380,998 | 4/1983 | Kieffer et al. | 218/9 |
| 4,527,896 | 7/1985 | Irani et al. | 356/43 |
| 4,602,642 | 7/1986 | O'Hara et al. | 128/664 |
| 4,634,294 | 1/1987 | Christol | 374/170 |
| 4,636,091 | 1/1987 | Pompei et al. | 374/124 |
| 4,662,360 | 5/1987 | O'Hara et al. | 128/9 |
| 4,772,612 | 2/1988 | Junkert et al. | 374/124 |
| 4,790,324 | 12/1988 | O'Hara et al. | 128/664 |
| 4,863,281 | 9/1989 | Suszynski | 374/158 |
| 4,895,164 | 1/1990 | Wood | 128/736 |
| 4,911,559 | 3/1990 | Meyst et al. | 374/158 |
| 4,932,789 | 6/1990 | Egawa et al. | 374/126 |

FOREIGN PATENT DOCUMENTS 0044791 7/1981 European Pat. Off. .
WO90/05902 5/1990 PCT Int'l Appl. .

Primary Examiner—Allan N. Shoap
Assistant Examiner—W. Morris Worth
Attorney, Agent, or Firm—Fulwider Patton Lee & Utecht

[57] ABSTRACT

The protective apparatus for a biomedical thermometer having a protruding probe containing a waveguide includes mounting a transparent window at the patient end of the waveguide to seal the waveguide from contamination while permitting infrared energy to pass. A protective sleeve protects and mounts the transparent window to the waveguide and material is provided along the entire probe-length of the waveguide to protect it. An outer boot is mounted over the transparent window and waveguide protection material to provide further protection and to supply a mounting and retaining surface for a protective probe cover. A disposable protective probe cover having a generally thin, flat, frame member with an aperture therethrough, is sized to fit over and be retained over the base of the probe by a friction interference fit. Extending across the aperture of the probe cover frame member is a material which stretches to generally conform to the shape of the probe when the tip of the probe is inserted through the aperture of the frame. A probe cover sensor is provided to indicate the existence of a protective probe cover.

22 Claims, 3 Drawing Sheets

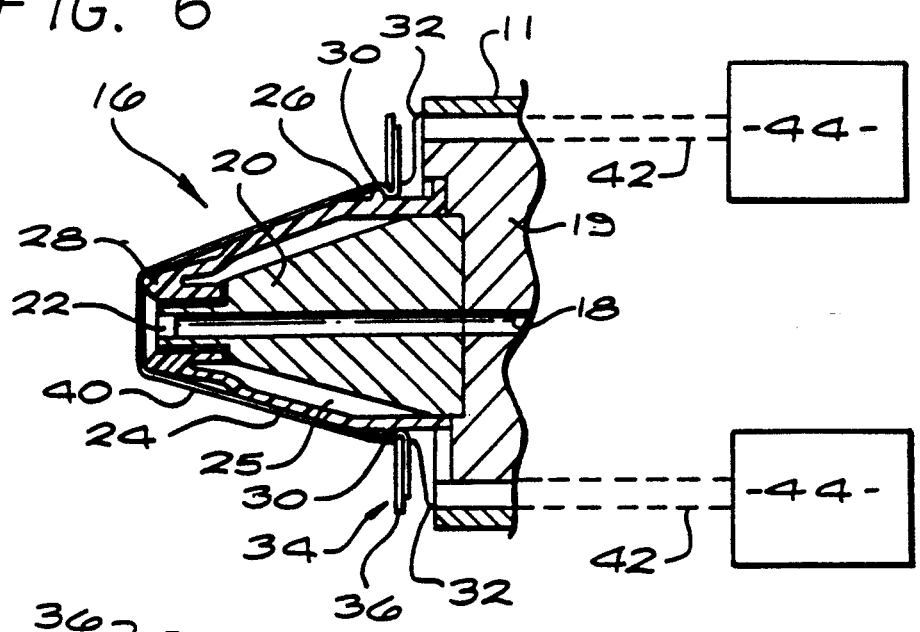
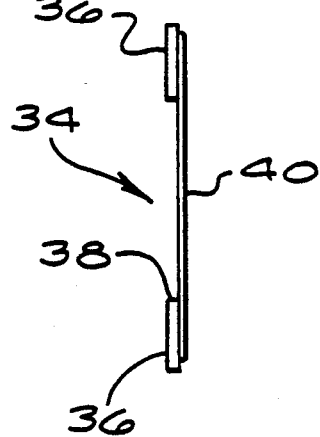
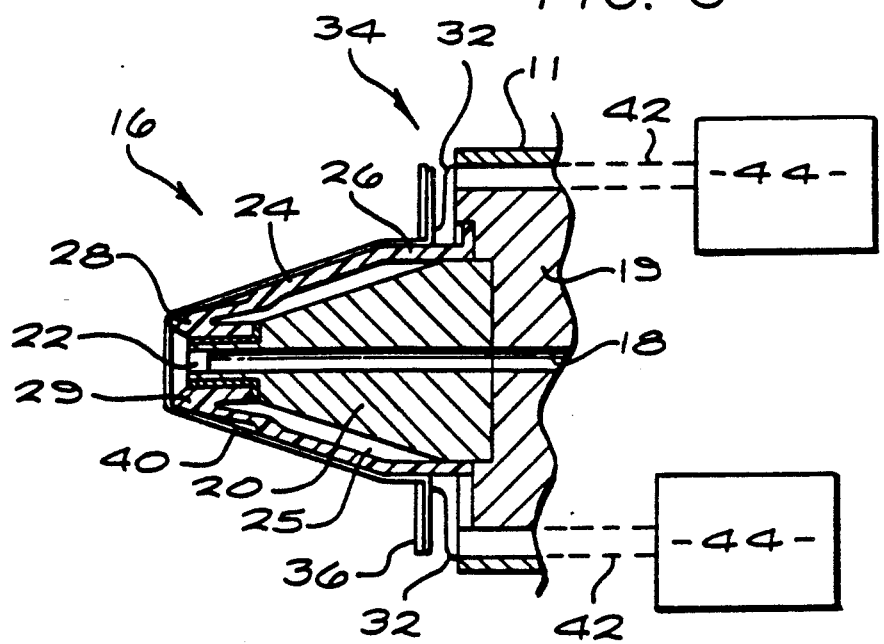

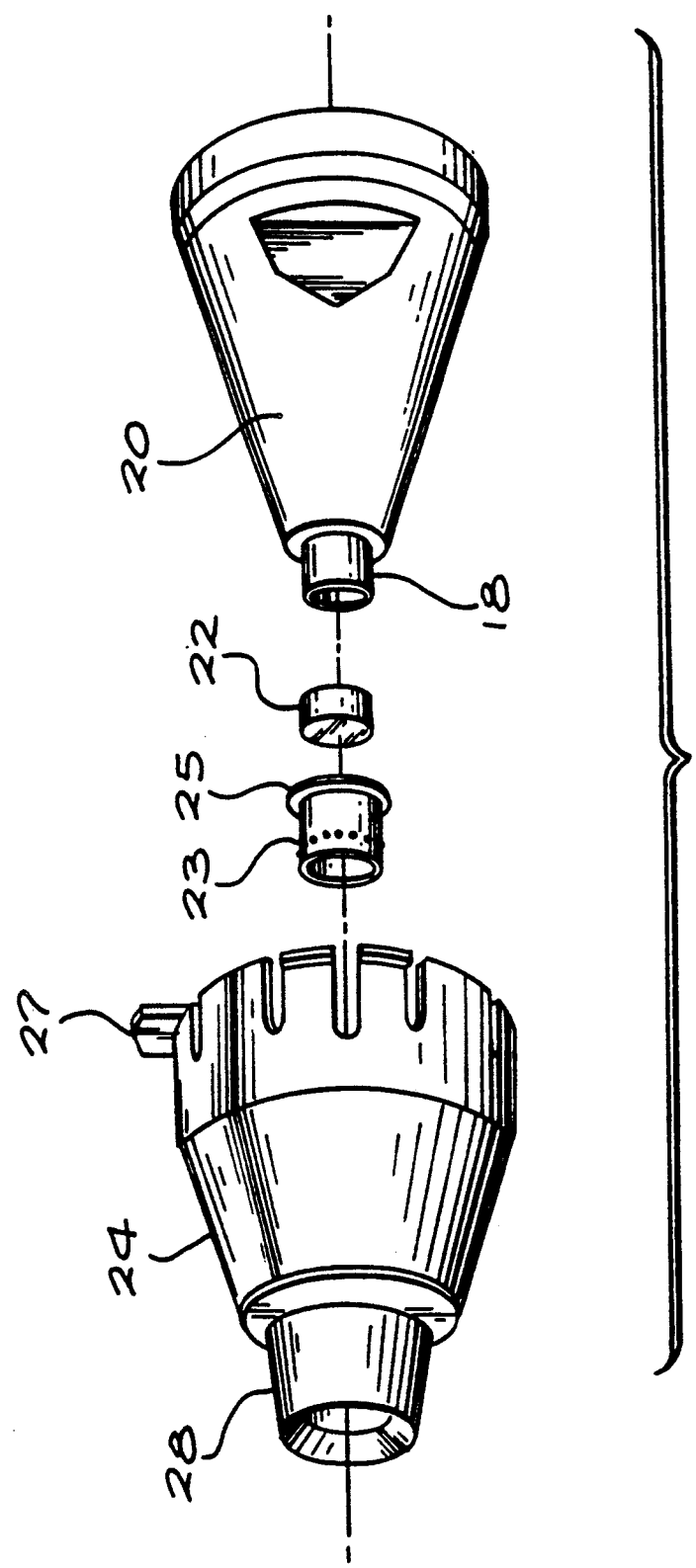

PROTECTIVE APPARATUS FOR A BIOMEDICAL PROBE

BACKGROUND OF THE INVENTION

1. Field of the Invention

This invention relates generally to a protective apparatus for biomedical instrumentation, and more particularly relates to a protective system for a probe of a biomedical thermometer.

2. Description of Related Art

Medical thermometers are useful in the diagnosis of many diseases. Infrared (IR) thermometers have recently become popular because they require less time and less patient manipulation to obtain an accurate measurement of a patient's temperature than conventional mercury or electronic thermometers.

Infrared biomedical thermometers are typically used to measure a patient's temperature from the auditory canal and the tympanic membrane. Typically, such a temperature measurement can be performed in a matter of a few seconds or less. However, such thermometers are sensitive to changes in the optical characteristics of the probe which may be caused by contamination, vibrational shocks or other causes. In some cases, a sheath or probe cover is used which is transparent to IR energy. The cover is fastened in some way over the part of the instrument directed at the patient's tympanic membrane. Reuse of such a cover may result in contamination accumulating on the cover and because the cover lies in the optical path of the thermometer, such contamination may result in inaccurate temperature measurements as well as causing cross contamination from patient to patient. Disposing of the probe cover after each temperature measurement assists in avoiding both the accumulation of contamination in the optical path and patient cross contamination.

While such a cover assists in protecting this part of the instrument from contamination, the cover typically provides little or no shock protection, such as in the case when the instrument is dropped. In the case of a probe containing a waveguide which forms part of the optical path, damage suffered by the waveguide as a result of rough handling could result in inaccurate temperature measurements. Distortion or bending, no matter how slight, may cause a significant change in the optical path. Additionally, the introduction of dirt, condensation or other contaminants into the waveguide can adversely affect its performance. There may be occasions when a disposable cover is not present over the waveguide distal end, thus without some other type of protection, dirt or other contaminants could enter the waveguide and interfere with its subsequent operation.

It would be desirable to provide a protective system for the probe of a thermometer, which would protect the parts, such as the waveguide of the probe, and which would also prevent contamination of the waveguide and other parts which may make contact with patients or operators of the instrument. For an infrared thermometer, it would also be desirable for a probe cover portion of such a system to be transparent to infrared radiation. In addition, to avoid inadvertent contamination, it would be further desirable for the protective apparatus to include a means for sensing the existence and correct positioning of the probe cover. The present invention addresses these needs.

SUMMARY OF THE INVENTION

The present invention provides a protective apparatus for a biomedical probe such as that used in an IR thermometer. It is particularly suitable to probes which have a waveguide and which are directed towards, and in some cases, are in contact with, a patient when used. A window is disposed at the probe end of the waveguide for sealing the waveguide so that contaminants do not enter. A sleeve surrounds the window and the end of the waveguide to mount them in their relative positions and to protect them from damage due to shocks. Additionally, further protective material is mounted along the entire length of the waveguide to protect it. In the embodiment shown herein, this further material comprises a heat sink surrounding the waveguide.

The protective apparatus also includes an outer boot formed of a durable material and mounted over the waveguide portion of the probe to further protect the waveguide and window from damage and to provide a base on which to mount a probe cover. The distal tip of the boot has a shape somewhat complementary to an ear canal so that the probe can be partially inserted into an ear canal for temperature measurements. In one embodiment, the outer boot includes knurling at the base of the boot for use in retaining a protective probe cover over the probe.

A disposable protective probe cover portion of the apparatus includes a generally flat frame member with an aperture therethrough, sized to fit over and be retained by an interference fit with the base of the boot. Extending across the aperture of the frame member is a material which streches to generally conform to the shape of the probe when the tip of the probe is inserted through the aperture of the frame. The disposable protective probe cover can be manufactured simply and inexpensively, and may be readily slipped over the end of the probe and then readily removed after use. This arrangement allows for an individual protective probe cover to be used for each patient to be examined, thereby permitting use of the same thermometer for multiple patients while preventing contamination between patients. The protective probe cover also prevents contamination of the waveguide transparent cover. In one embodiment, one or more position sensors are mounted in the body of the thermometer to detect the positioning of the disposable protective probe cover over the probe, and to generate a signal which may be used to prevent use of the thermometer if the probe cover is not in place.

Other aspects and advantages of the invention will become apparent from the following detailed description, and the accompanying drawings, which illustrate by way of example the features of the invention.

BRIEF DESCRIPTION OF THE DRAWINGS

FIG. 3 is a partial sectional view through the axis of the probe of the thermometer shown in FIG. 1;

FIG. 4 is an exploded view of the probe assembly;

FIG. 5 is a side elevational view of the disposable protective probe cover portion of the protective apparatus of the invention with the film in its unextended shape;

FIG. 6 is a view similar to that of FIG. 3, showing an alternate embodiment of the outer boot of the protective apparatus of the invention.

DETAILED DESCRIPTION OF THE PREFERRED EMBODIMENT

As shown in the exemplary drawings, the invention is embodied in a protective apparatus usable with a biomedical thermometer having a body portion and a protruding probe having a waveguide extending through the probe for receiving and channeling infrared radiation to an infrared detector located in the body portion.

Figure 1:
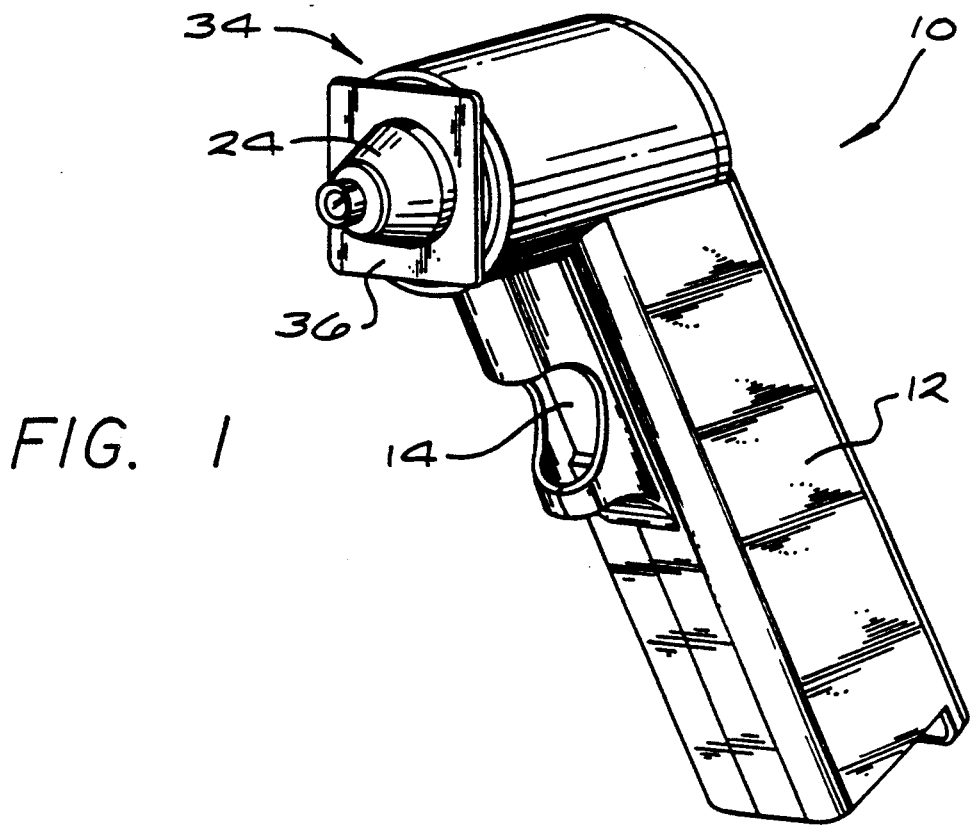
FIG. 1 is a front perspective view of a biomedical thermometer with the protective apparatus in place over the tip of the probe of the thermometer.
Figure 2:
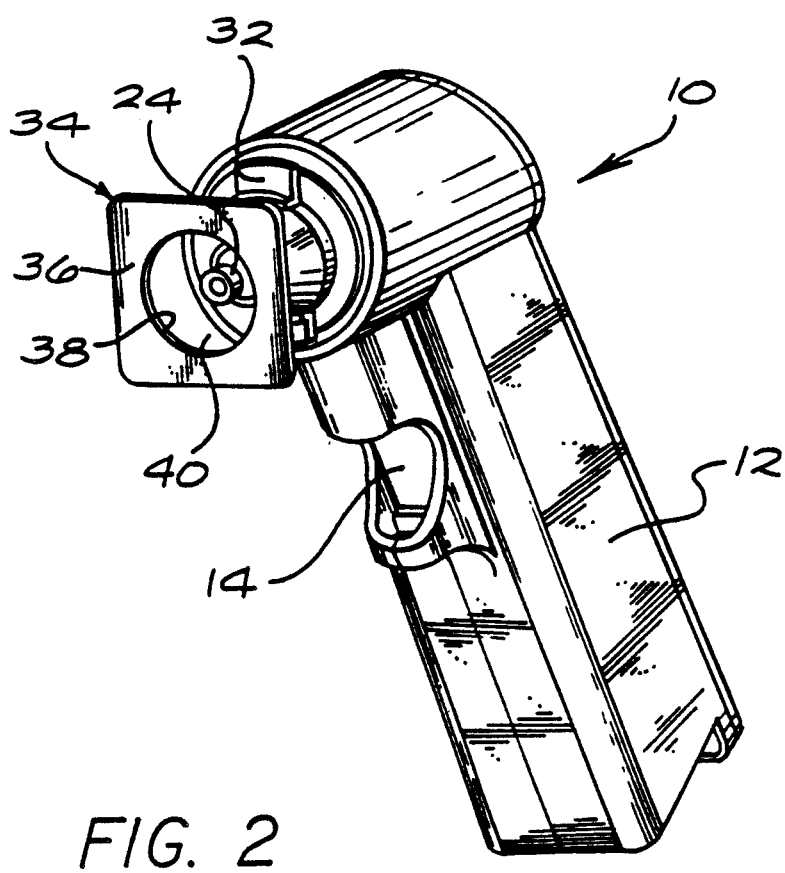
FIG. 2 is a view of the biomedical thermometer showing how the disposable protective probe cover fits over the probe of the thermometer.

Referring now to FIGS. 1 through 3, an infrared biomedical thermometer 10 for sensing the temperature of a patient is shown. The body of the biomedical thermometer 11 (FIG. 3) houses an infrared detector (not shown), and functional elements necessary for determination of the temperature of the patient based upon the infrared radiation received by the thermometer from a body cavity such as the ear canal, or other portions of the patient's anatomy. As used in this description, the infrared radiation referred to generally has a range of wavelengths of from 7 to 15 microns. The thermometer is preferably a hand held type including a handle 12, and an on-off trigger switch 14, so that the temperature readings may be quickly taken by the user by pointing the protruding probe 16 end at the portion of the patient from which a temperature reading is to be taken. The probe 16 typically includes a waveguide portion 18, which in this embodiment is generally cylindrical in shape and extends axially through the probe 16 to the infrared detector (not shown), for communication of infrared energy from the temperature source to the infrared detector. Although a generally cylindrically shaped waveguide is shown in this embodiment, this is for illustration purposes only. Other shapes of waveguides may be used. For example, in one embodiment, a slightly frustro-conically shaped waveguide was found to be the most useful. The larger opening of the waveguide was at the distal end of the probe, while the smaller waveguide opening was located next to the IR detector. This configuration resulted in more IR energy from the patient reaching the detector.

Surrounding the waveguide 18 is a heat sink 20. The heat sink 20 may be integral with the waveguide 18 or may merely be in contact with the waveguide 18. In the embodiment shown in FIG. 3, the heat sink 20 is first formed and then a channel is formed through it for locating the waveguide 18. The channel is then coated with a highly reflective substance such as gold to form the finished waveguide 18.

Referring now to FIG. 4, a window 22 is disposed at the end of the waveguide 18, and is mounted and protected in a sleeve 23 placed over the distal tip of the waveguide 18 and the window 22. The window 22 may be formed of a glass-like material such as zinc selenide which is substantially transparent to infrared energy. Alternatively the window could be made of polyethylene, or other similar materials that are also substantially transparent to infrared energy. In the embodiment disclosed, the zinc selenide lens is used to pass the infrared energy while sealing the end of the waveguide from contaminants. The sleeve 23 is preferably generally tubular and is made of a rugged material such as stainless steel to protect the window. Additionally, the material is chosen to have a low thermal conductivity to provide additional insulation for these same two elements. In one embodiment, low thermal conductivity stainless steel was used. The sleeve may also include a flange 25 at one end to fit snugly against a corresponding inset portion of the heat sink 20. The sleeve 23 preferably includes a lip around the inside of the end of the sleeve away from the flange end 25 for retention of the window during assembly, and a series of holes around the lip end of the sleeve through which adhesive may be applied to the edge of the window to permanently bond it in place in the sleeve 23. The sleeve and window can therefore readily be removed and replaced if the window is broken by sliding them off the end of the waveguide 18.

The sleeve 23 also provides protection for the waveguide 18 at the narrow distal end of the probe itself from vibrational shocks and abrasions which could otherwise be detrimental to the performance of the waveguide and in turn of the thermometer. The window 22 serves to prevent clogging or contamination of the waveguide 18 by ear wax, dirt, moisture, or other material which could interfere with uniformity and consistency of temperature readings by thermometer. The remainder of the waveguide is protected by the heat sink.

While the sleeve 23 provides some protection of the window 22 and waveguide 18 end by being formed of a hard material such as stainless steel, it may not provide enough protection of the window and waveguide end when the thermometer is subjected to harsher operating conditions, such as when it is dropped onto a floor or a counter. Additional protection would be desirable. The outer boot 24 portion of the protective system of the invention provides additional protection.

Referring again to FIGS. 3 and 4, the outer boot 24 contacts the heat sink 20 at the proximal base portion 26 of the boot, and at the distal tip portion 28 of the boot. The outer boot 24 is typically 2.54 mm (0.10 in.) thick and is preferably formed of a durable material such as ABS, which is well known for its durability and protective properties; although other plastic or elastomeric materials would also be suitable. A closed air space or air gap 25 of approximately 0.8 mm (0.03 in.) may be formed between the boot 24 and the heat sink 20, to provide a layer of insulative air around the waveguide to protect the waveguide channel and window from transient changes in ambient temperature outside of the probe. One or more tabs 27 are provided for mounting the boot 24 to corresponding slots (not shown) in the body 11 of the thermometer. Other means of attachment may be used as apparent to those skilled in the art. The distal tip 28 of the boot 24 is preferably involuted to form an inwardly folded extension 29 which slips over the sleeve 23 holding it in position on the distal end of the waveguide 18.

The base portion 26 of the boot 24 preferably includes a roughened or textured surface to accept a probe cover frame and which serves to positively retain the probe cover frame in place over the outer boot. The roughened surface may be formed by sandblasting or by molding the surface as such or by other means. The boot may be roughened in other ways such as by adding a rough substance to the boot at the base portion 26 to assist in retaining the disposable probe cover.

Referring now to 1, 2, 3, and 5, the probe cover 34 typically includes a thin, flat, frame member 36, which includes a central aperture 38 sized to fit over the base portion 26 of the boot 24, which receives the protective probe cover and retains the probe cover in place by an interference fit with the probe cover frame 36. FIG. 1 shows the probe cover in place on the probe and FIG. 2 shows the probe cover at the distal end of the probe prior to fitting it onto the probe. The frame member 36 is preferably made from a deformable, thin cardboard, which can be crushed slightly as it is applied to fit snugly over the outer boot 24 of the probe. The frame member 36 could also be made from plastic, metal, wood, or other material. Because the probe cover is meant to be disposable, it may be permanently deformed, such as by partially crushing the frame during installation. Other techniques for holding the frame in place on the probe cover 24, such as by clamping, are also usable. A stretchable plastic film 40 is attached to one side of the probe cover frame member 36 across the aperture 38, so that as the probe cover is placed over the outer boot, the film stretches to seal the probe against contamination, and conforms to the general shape of the outer boot 24 of the probe.

The stretchable plastic film 40 is preferably made of a low or ultra-low density polyethylene which can stretch to several times its original length without rupturing or tearing, and which is substantially transparent to infrared radiation. Also, linear low density polyethylene may be usable. Other stretchable infrared materials which would similarly form an infrared transparent sheath may also be suitable. The stretchable film is attached to the frame member either by a chemical adhesive, heat sealing, ultrasonic sealing, or by other means.

Another protective means provided is a probe cover sensor. The sensor is used to determine the existence of a probe cover 34 on the probe 16. In the embodiment shown in FIGS. 2 and 3, one or more movable probe cover sensor buttons 32 are provided in the body 11 of the thermometer. The probe cover sensor buttons 32 are movable axially away from the probe 16 by the disposable protective probe cover frame 36 when it is placed over and retained on the boot 24. The probe cover sensor buttons 32 are biased to extend toward the tip of the probe 16 by extension springs (not shown) or other means located in the body of the thermometer. When the protective probe cover 34 is thus received on the boot 24, the movable probe cover-sensors are displaced axially away from the distal probe tip by the probe cover, moving corresponding contact switch activator members 42 to cause a contact switch 44 to provide an electrical signal indicating proper placement of the probe cover 34. Other types of switches, such as an optical switch may be used. Such a signal may be used in the operation of the thermometer, such as by requiring its existence before a temperature reading can be taken. In another embodiment, the probe cover sensors 32 may be used to disable the thermometer until the used probe cover has been removed and replaced with another.

In another embodiment of the protective system in accordance with the invention as illustrated in FIG. 6, the outer boot includes a base portion with at least one annular raised rib 30. The protective probe cover 34 is fitted over the outer boot and retained in a manner substantially identical to that illustrated in FIG. 3, except that an annular rib 30 is provided for positive retention of the protective probe cover. In another embodiment, a plurality of annular raised ribs may be used to compensate for manufacturing tolerances. Other embodiments which secure the probe cover in a fixed position in relation to the probe 16 by means of an interference fit are possible.

It will be apparent that the protective system of the invention is not limited to use with infrared thermometers, and may be used with other instruments having a probe portion for which protection would be advantageous.

While several particular forms of the invention have been illustrated and described, it will be apparent that various modifications can be made without departing from the spirit and scope of the invention. Accordingly, it is not intended that the invention be limited, except by the appended claims.

I claim:

1. A hand-held biomedical apparatus comprising:
a probe having a distal end for being directed at a patient and a base portion for use in retaining a probe cover on the probe; and
protection means for protecting the probe, the protection means comprising a protective probe cover having a frame member formed of a permanently deformable, nonresilient material, the frame member having an aperture sized such that it is smaller than the base portion but is sized to fit over the base portion of the probe and to be retained in a fixed position on the base portion by a friction interference fit, the probe cover having a stretchable material attached to the probe cover frame member and extending across the aperture such that when the distal end of the probe is inserted through the aperture to fit the probe cover frame member over the base portion, the material will stretch to conform generally to the shape of the probe.

2. The biomedical apparatus of claim 1 wherein:
the probe further comprises a waveguide formed through the probe and opening at the distal end for receiving energy from the patient and conducting the energy through the probe; and
the protection means further comprises waveguide protection means for providing material around the waveguide along its entire length and at its distal end opening for protecting the waveguide.

3. The biomedical apparatus of claim 2 wherein the waveguide protection means comprises an outer boot formed of a shock absorbent material mounted over and surrounding the waveguide along its length on which is formed the base portion for mounting the frame member and which forms the outer surface of the probe to which the stretchable material conforms.

4. The biomedical apparatus of claim 2 wherein the waveguide protection means further comprises window means for sealing the opening of the waveguide at the distal end against contaminants while being transparent to the energy to be received by the waveguide.

5. The biomedical apparatus of claim 4 wherein the waveguide protection means comprises a sleeve mounted over the window means and the distal end of the waveguide for protecting the window means and waveguide from physical shocks.

6. The biomedical apparatus of claim 2 wherein the protection means further comprises:
window means for sealing the opening of the waveguide at the distal end against contaminants while being transparent to the energy to be received by the waveguide;
a sleeve mounted over the window means and the distal end of the waveguide for protecting the window means and waveguide from physical shocks; and an outer boot formed of a shock absorbent material and mounted over the waveguide along its entire length on which is formed the base for mounting the frame member and which forms the outer surface of the probe to which the stretchable material conforms.

7. A hand-held biomedical apparatus comprising:
a probe having a distal end for being directed at a patient and a base portion; and
protection means for protecting the probe, the protection means comprising a protective probe cover having a frame member with an aperture sized to fit over the base portion of the probe and to be retained in a fixed position in relation to the base portion by interference fit, the probe cover having a stretchable material attached to the probe cover frame member and extending across the aperture such that when the distal end of the probe is inserted through the aperture to fit the probe cover frame member over the base portion, the material will stretch to conform generally to the shape of the probe; and
the protection means further comprises sensor means for sensing the presence of the protective probe cover at the fixed position on the probe and for providing a signal responsive to the sensing.

8. The biomedical apparatus of claim 1 wherein the base portion includes a roughened surface area to receive the probe cover and to positively retain the probe cover in place over the base portion by the friction between the roughened surface area and the probe cover.

9. The biomedical apparatus of claim 1 wherein the probe cover frame member comprises permanently deformable cardboard and the aperture is sized to be smaller than the size of the base.

10. A hand-held biomedical apparatus comprising:
a probe having a distal end for being directed at a patient and a base portion for use in retaining a probe cover on the probe and having a uniform cross-section along its length and comprising a waveguide formed through the probe and opening at the distal end for receiving energy from the patient and conducting the energy through the probe;
protection means for protecting the probe, the protection means comprising a protective probe cover having a frame member formed of a permanently deformable, nonresilient material, the frame having an aperture sized such that it is smaller than the base portion but is sized to fit over the base portion of the probe and to be retained in a fixed position in relation to the base portion by a friction interference fit, the probe cover having a stretchable material attached to the probe cover frame member and extending across the aperture such that when the distal end of the probe is inserted through the aperture to fit the probe cover frame member over the base portion, the material will stretch to conform generally to the shape of the probe; and
the protection means further comprising waveguide protection means for providing material around the waveguide along its entire length and at its distal end opening for protecting the waveguide, the waveguide protection means comprising an outer boot formed of a shock absorbent material and mounted over and surrounding the waveguide along its length on which is formed the base portion for mounting the frame member and which forms the outer surface of the probe to which the stretchable material conforms.

11. The biomedical apparatus of claim 10 wherein the waveguide protection means further comprises window means for sealing the opening of the waveguide at the distal end against contaminants while being transparent to the energy to be received by the waveguide.

12. The biomedical apparatus of claim 11 wherein the waveguide protection means further comprises a sleeve mounted over the window means and the distal end of the waveguide for protecting the window means and waveguide from physical shocks.

13. The biomedical apparatus of claim 10 wherein the waveguide protection means further comprises:
window means for sealing the opening of the waveguide at the distal end against contaminants while being transparent to the energy received by the waveguide;
a sleeve mounted over the window means and the distal end of the waveguide for protecting the window means and waveguide from physical shocks; and
the outer boot is mounted over the window means, the sleeve and the waveguide along its length.

14. A hand-held biomedical apparatus comprising:
a probe having a distal end for being directed at a patient and a base portion and comprising a waveguide formed through the probe and opening at the distal end for receiving energy from the patient and conducting the energy through the probe;
protection means for protecting the probe, the protection means comprising a protective probe cover having a frame member with an aperture sized to fit over the base portion of the probe and to be retained in a fixed position in relation to the base portion by interference fit, the probe cover having a stretchable material attached to the probe cover frame member and extending across the aperture such that when the distal end of the probe is inserted through the aperture to fit the probe cover frame member over the base portion, the material will stretch to conform generally to the shape of the probe;
the protection means further comprising waveguide protection means for providing material around the waveguide along its entire length and at its distal end opening for protecting the waveguide, the waveguide protection means comprising an outer boot mounted over and surrounding the waveguide along its length on which is formed the base portion for mounting the frame member and which forms the outer surface of the probe to which the stretchable material conforms and window means for sealing the opening of the waveguide at the distal end against contaminants while being transparent to the energy received by the waveguide and a sleeve mounted over the window means and the distal end of the waveguide for protecting the window means and waveguide from physical shocks and the outer boot is mounted over the window means, the sleeve and the waveguide along its length; and
the protection means further comprises sensor means for sensing the presence of the protective probe cover at the fixed position on the probe and for providing a signal responsive to the sensing.

15. The biomedical apparatus of claim 13 wherein the base portion includes a roughened surface area to receive the probe cover and to positively retain the probe cover in place over the base portion by the friction between the roughened surface area and the probe cover.

16. The biomedical apparatus of claim 13 wherein the probe cover frame member comprises permanently deformable cardboard and the aperture is sized to be smaller than the size of the base.

17. A hand-held biomedical apparatus for receiving infrared energy comprising:
   a probe having a distal end for being directed at a patient and a base portion for use in retaining a probe cover on the probe, the base portion having a uniform cross-section along its length and a roughened surface area, and comprising a waveguide formed through the probe and opening at the distal end for receiving infrared energy from the patient and conducting the energy through the probe;
   protection means for protecting the probe comprising a protective probe cover having a generally flat frame member formed of a permanently deformable, nonresilient material, the frame having an aperture sized such that it is smaller than the base portion but is sized to fit over the base portion of the probe and to be retained thereon by a friction interference fit with the roughened surface area of the base portion, the probe cover having a stretchable material attached to the probe cover frame member and extending across the aperture such that when the distal end of the probe is inserted through the aperture to fit the probe cover frame member over the base portion, the material will stretch to conform generally to the shape of the probe, the stretchable material disposed in relation to the frame member such that when the probe cover is in place on the probe, the frame member is disposed between the stretchable material and the distal end of the probe; and
   the protection means further comprising waveguide protection means for providing material around the waveguide along its entire length and at its distal end opening for protecting the waveguide, the waveguide protection means comprising window means for sealing the opening of the waveguide at the distal end against contaminants while being transparent to infrared energy to be received by the waveguide and a sleeve mounted over the window means and the distal end of the waveguide for protecting the window and waveguide from physical shocks, and further comprising an outer boot formed of shock absorbent material and mounted over and surrounding the waveguide along its length on which is formed the base portion for mounting the frame member and which forms the outer surface of the probe to which the stretchable material conforms.

18. A hand-held biomedical apparatus for receiving infrared energy comprising:
   a probe having a distal end for being directed at a patient and a base portion and comprising a waveguide formed through the probe and opening at the distal end for receiving infrared energy from the patient and conducting the energy through the probe;
   protection means for protecting the probe comprising a protective probe cover having a generally flat frame member with an aperture sized to fit over the base portion of the probe and to be retained thereon by interference fit with the base portion, the probe cover having a stretchable material attached to the probe cover frame member and extending across the aperture such that when the distal end of the probe is inserted through the aperture to fit the probe cover frame member over the base portion, the material will stretch to conform generally to the shape of the probe;
   the protection means further comprising waveguide protection means for providing material around the waveguide along its entire length and at its distal end opening for protecting the waveguide, the waveguide protection means comprising window means for sealing the opening of the waveguide at the distal end against contaminants while being transparent to infrared energy to be received by the waveguide and a sleeve mounted over the window means and the distal end of the waveguide for protecting the window and waveguide from physical shocks, and further comprising an outer boot mounted over and surrounding the waveguide along its length on which is formed the base portion for mounting the frame member and which forms the outer surface of the probe to which the stretchable material conforms; and
   the protection means further comprises sensor means for sensing the presence of the protective probe cover on the base portion of the probe and for providing a signal responsive to the sensing.

19. The biomedical apparatus of claim 17 wherein the roughened surface area of the base portion includes a rough material applied to the base portion.

20. The biomedical apparatus of claim 17 wherein the roughened surface area of the base portion is formed into the base portion.

21. The biomedical apparatus of claim 8 wherein the roughened surface area of the base portion comprises a rough material applied to the base portion.

22. The biomedical apparatus of claim 8 wherein the roughened surface area of the base portion is formed into the base portion.

* * * * *